United States Patent [19]

Nixon

[11] 4,061,033
[45] Dec. 6, 1977

[54] TEMPERATURE FUNCTION INTEGRATOR

[75] Inventor: Peter Anthony Nixon, Wellington, New Zealand

[73] Assignee: Development Finance Corporation, New Zealand

[21] Appl. No.: 664,475

[22] Filed: Mar. 8, 1976

[30] Foreign Application Priority Data

Mar. 10, 1975 New Zealand .................. 176879

[51] Int. Cl.² .................. G01D 1/04; G01D 3/02; G01N 33/02
[52] U.S. Cl. .................. 73/339 R; 73/362 AR
[58] Field of Search .......... 73/362 AR, 339 R, 343.5; 426/88

[56] References Cited

U.S. PATENT DOCUMENTS

| | | | |
|---|---|---|---|
| 2,505,521 | 4/1950 | Boyajian | 73/350 X |
| 2,972,253 | 2/1961 | Benson | 73/339 R X |
| 3,045,488 | 7/1962 | Jurs et al. | 73/362 AR X |
| 3,561,270 | 2/1971 | Sessler | 73/362 AR |
| 3,645,804 | 2/1972 | Ponchez | 73/362 AR X |
| 3,911,374 | 10/1975 | Busse et al. | 73/362 AR X |
| 3,911,746 | 10/1975 | Spangler et al. | 73/362 AR X |

Primary Examiner—James J. Gill
Attorney, Agent, or Firm—Holman & Stern

[57] ABSTRACT

The temperature function integrator disclosed senses the temperature of a temperature sensitive food and provides as an output a measure of the food deterioration. A temperature transducer produces an electrical signal which is modified according to a transfer function simulating the temperature — rate of deterioration relation for the food by either analogue or digital means. The modified signal determines the pulse rate or the number of pulses generated at a sample time by a pulse generator, and these pulses are counted by a digital counter which performs an integrating function. A number of counters can be used to give deterioration for a number of selected temperature ranges. An integral or remote read-out decodes the counter. Rate of deterioration and absolute deterioration information may be telemetered to a remote receiver and read-out.

8 Claims, 4 Drawing Figures

TEMPERATURE FUNCTION INTEGRATOR

BACKGROUND OF THE INVENTION

This invention relates to a temperature function integrator and in particular but not solely to such an instrument for use in providing an indication of the deterioration of stored material.

It is well known that food stuffs in particular and in addition many other materials, deteriorate in storage and that the rate of deterioration is less at lower temperatures. (Olley and Ratkowsky, "Temperature function integration and its Importance in the Storage and Distribution of Flesh Foods above Freezing Point", *Food Technology in Australia*, Vol. 25 No. 2, February 1973, pp 66–73). This is particularly true of fish. Three different temperature zones are recognized for the storage of fish, see FIG. 1. At temperatures above $-1°$ C and below ambient fish is termed chilled and no water in the fish tissue is in the form of ice crystals. At low temperatures about 31 18° C the fish is termed frozen and most of the water in fish tissue is in the form of ice crystals with the result that the concentration of solutes in the liquid phase prevents the growth of spoilage bacteria. In the course of freezing, the physical effects of ice crystal growth normally occur from the time the tissue is at $-1°$ until the tissue is at $-5°$ C. The temperatures zone $-1°$ to $-5°$ C, when the tissue is partially frozen, is sometimes referred to as superchilled. (Kreuzer (ed.) *Freezing and Irradiation of Fish* (1969) Fishing News (Books) Ltd., London pp 101–127.). The super-chilled region is always encountered by frozen fish, is sometimes encountered accidentally in the storage of chilled fish and is sometimes used to store fish for longer periods than can be used with the chilled region. It is common for fishing vessels to be equipped with fish holds cooled by ice or other forms of refrigeration which can achieve a combination of chilling, superchilling and freezing. (Nixon, Paper delivered by P A Nixon to the New Zealand Fishing Industry Board's seminar on Quality in Fish Products, Wellington, Aug. 17 - 18, 1971.). For each temperature zone, chilled, superchilled, and frozen, there are relations linking the rate of deterioration or the useful storage life to the temperature of storage. For instance, a fish which will remain edible for about 1 day at 20° C will keep for about 10 days at 0° C and will keep for about 100 days when deep frozen at $-20°$ C.

In order to investigate, to control or to assess the effects of the storage conditions of fish and the effectiveness of various methods of refrigeration, it is clearly not sufficient to measure only the time of storage or even the average temperature of storage. Known devices for integrating the average temperature of a material with time give information of only limited use. It is necessary to take into account the length of time that a fish has been held at any particular temperature and it is desirable to know the extent of deterioration which has occurred in the chilled, superchilled, and frozen temperature zones respectively. This can be done by recording the temperature of fish on a chart recorder or by other means multiplying the indication of temperature by a factor which embodies the rate of deterioration at the temperature in question, preparing a new record of modified temperature against time and commonly integrating over the time of storage. Such a procedure has been recommended for assessing the quality of stored frozen foods (*Recommendations for the Processing and Handling of Frozen Foods;* International Institute of Refrigeration 1964, pp 50–52.) This is a very time consuming process and one that is impractical to apply in most circumstances. In practice it is complicated by the fact that it is now known that the temperature indicators normally fitted in fishing vessels to indicate the temperature of the fish hold do not give the required information. It is reported by Nixon (l.c.) that the temperature of the air in the fish hold is by no means identical with the temperature of the fish.

SUMMARY OF THE INVENTION

It is therefore an object of the present invention to provide an instrument for assessing the deterioration of stored material which has a rate of deterioration which is a function of temperature which will go some way to overcoming the abovementioned difficulties.

Accordingly the invention consists in a temperature function integrator. A transducer senses temperature in a material to be monitored and produces an electrical signal proportional to the sensed temperature. A signal modifier accepts the transducer signal and modifies it according to a predetermined transfer function to produce a quantity the value of which corresponds to the instantaneous rate of deterioration of the monitored material. An integrator integrates the output of the signal modifier with respect to time, the integral value being stored upon the monitoring period being terminated. A display is provided to produce a read-out of the integral value which is a measure of the deterioration of the monitored material up to the time of reading.

In order to provide a measure of the deterioration or spoilage, the instrument of the present invention makes use of the fact that the rate of deterioration or spoilage is a function of temperature. Since temperature can be sensed and an electrical analogue readily produced, an electrical analogue of rate of deterioration is obtained by modifying the temperature analogue using either digital or analogue electronic circuitry set up to produce an electrical output which is a predetermined function of the input. The resulting electrical quantity is then integrated with respect to time by a suitable electronic integrator, the output of which is representative of the absolute deterioration or spoilage.

In one preferred form of the invention, an electrical current is derived which has an instantaneous value directly proportional to the rate of deterioration of the material being measured. Integration is achieved by using this current to control the pulse rate of a pulse generator such that with increasing current corresponding to increasing spoilage rate the pulse rate is increased in proportion. The pulse generator feeds a digital counter, the count of which is representative of the integral of the current controlling the pulse generator.

In a second preferred form of the invention, the electrical analogue produced by the temperature sensor is converted to digital form and subsequent processing is entirely digital. In this case modification according to the temperature-rate of deterioration relationship is carried out using a programmable read only memory which for each temperature value produces a new number in digital form which corresponds to the rate of deterioration. This digital data is converted from parallel to serial form by gating the pulses from a clock pulse generator, the gate enabling period being determined by the time taken for a down counter storing the PROM output number to be reset to zero. Accordingly at preset sample times a train of pulses is generated, the number of pulses in each train being proportional to the rate of deterioration at the time of the sample. These pulses are fed into a digital counter as in the first preferred form of the invention with the count being representative of the integral of the modified temperature data.

BRIEF DESCRIPTION OF THE DRAWINGS

Preferred forms of the invention will now be described with reference to the accompanying drawings in which.

DETAILED DESCRIPTION OF THE PREFERRED EMBODIMENTS OF THE INVENTION

Figure 1:
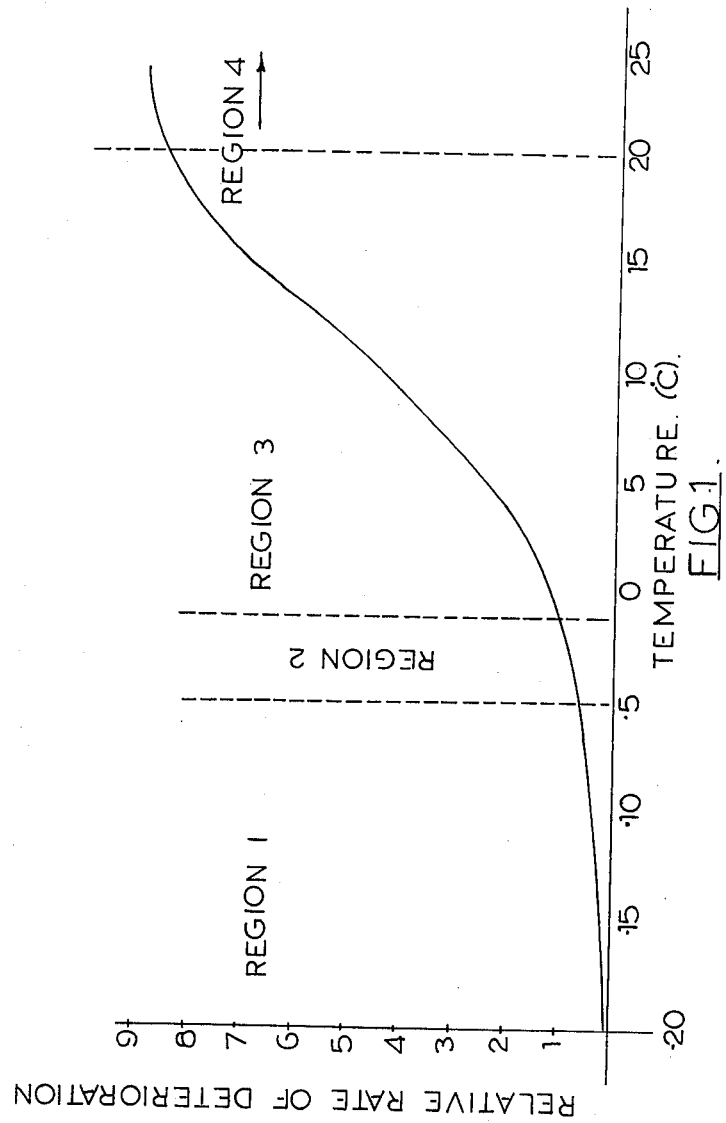
FIG. 1 is a graph showing the relation between the rate of deterioration of fish and temperature.

FIG. 1 shows the rate of deterioration of fish as a function of temperature. The relative rate of deterioration shown on the ordinate of FIG. 1 is rate of deterioration normalised to a rate of unity at 0° C. In region 1 below −5° C fish is in the frozen state and spoilage is a slow process caused mostly by chemical reactions. Data for region 1 has been taken from IIR 1964 (1.c.) p.50 Curve 6. In region 2 from −5° to −1° C fish is in the partially frozen or superchilled state where spoilage is caused by a combination of chemical and bacterial effects. Spoilage rates for region 2 has been interpolated from data in regions 1 and 3. Region 3 at temperatures from −1° to +20° C is the chilled temperature zone where fish spoilage is due largely to bacterial growth and where temperature control is of most practical value for preventing spoilage. In region 4, above 20° C, spoilage occurs at a rapid rate but is less affected by temperature. Data for regions 3 and 4 are from Olley and Ratkowsky (1.c.) FIG. 3C.

The first example of the temperature function integrator to be described is a model for determining spoilage when the greatest part of spoilage occurs in the chilled region above 0° C. In this case it is unnecesssary to include signal conditioning means for accurately simulating the curve of FIG. 1 in regions 1 and 2 in the same manner as the curve is simulated in regions 3 and 4. It has been found satisfactory and convenient to approximate a curve such as that in FIG. 1 by causing control in region 1 to be primarily due to the load presented by the detector of temperature. In region 2 a first simulating circuit is brought in. In region 3 a second simulating circuit is brought in and in region 4 a third simulating circuit is brought in.

Figure 2:
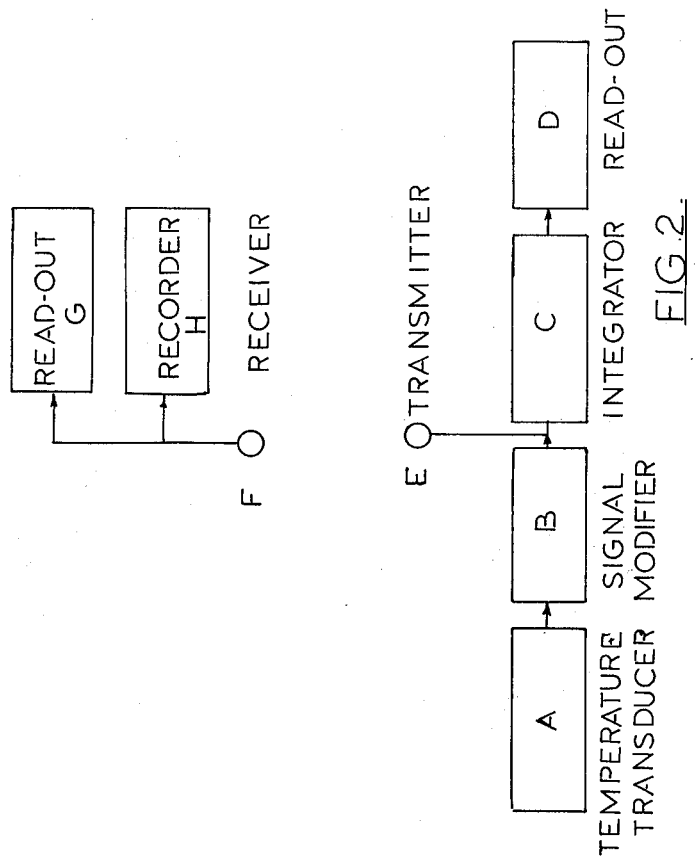
FIG. 2 is a block diagram of one form of temperature function integrator.

A block diagram of this temperature function integrator is shown in FIG. 2 wherein A represents a temperature sensor, B represents a signal modifier or function shaper, C represents an integrator and store, and D a readout of integrated modified temperature. E is an optional transmitter of modified temperature information. F is a remote receiver tuned to the frequency of transmitter E and may optionally feed a modified temperature read-out G or a tape recorder H, the latter being useful in investigative work. In the circuit diagram of FIG. 3, blocks A and B of FIG. 2 are shown within broken lines. The temperature sensor A is remote from the other units and in use is embedded in the material the deterioration of which is to be assessed. The sensor is connected to the other units, which are housed in an appropriate case, by a short lead. The read-out D may be integral with units B and C or, more advantageously constructed as a separate instrument which may be used to display the integrator value (the degree of deterioration or spoilage) of any number of temperature function integrators as and when readings are required. This would normally be at the end of the storage or transport time of the associated food.

The controlling feature is the type of temperature sensor shown at A. The present example uses a nominal 47 kohm (at 25° C) NTC thermistor set in the end of a 13 gauge hypodermic needle. The resistance of such a thermistor changes from about 150 kohms at 0° C to about 50 kohms at 20° C. With 18 volts on the positive rail (FIG. 2) and R1 140 kohms the total value of resistors R2, R4, R5, R6 and the shunted thermistor at 3 is adjusted so that the voltage across the thermistor is approximately 2 volts.

At this voltage the current through the thermistor changes with temperature from approximately 13 microamps at 0° C to approximately 40 microamps at 20° C. The configuration of T1 is such that alpha times this current flows in the collector of T1 and develops a voltage across D2 and R7. Alpha refers to the common base transistor parameter which has nearly enough a constant value of unity. R7 is of the order to 150 kohms so that the voltage at the bases of transistors 2, 3 and 4 changes from approximately 2.4 V at a thermistor temperature of 0° C to approximately 6.6 V at a thermistor temperature of 20° C. According to the thermistor temperature, one or all of the bases of transistors 2, 3 and 4 are forward biased so as to conduct, or reverse biased so as not to conduct. T4 alone conducts at temperatures below 0° C corresponding to the regions 1 and 2 in FIG. 1. This temperature range is below chilled temperature and the thermistor response alone is considered to be sufficiently sensitive for the occasions when such temperatures are encountered. R10 is adjusted so that the collector current of T4 has the desired value of 0° C; 8 megohms and 0.5 microamps respectively are convenient values. R5 is adjusted so that transistor 3 starts to conduct at 0° C. R9 is adjusted to control the emitter current and hence the collector current of T3 so that the total collector currents of T3 and T4 simulate FIG. 1 in region 3. Resistors R4 and R8 are adjusted in the same manner as resistors R5 and R9 respectively so that transistor T2 conducts in the region 4 of FIG. 1.

Resistors R11, R12, and R13 are adjusted to saturate transistors T2, T3 and T4 respectively at temperatures where the respective collector currents of these transistors are not required to change with the temperature in order to simulate FIG. 1.

Although only the transistors T2, and T3 are shown in this example, a larger number could be similarly incorporated to achieve closer simulation of the desired function, and/or to simulate the desired function over an extended temperature range.

The total collector current of transistors T2, T3 and T4 flows through the combination of transistors T5, diode D3 and resistors R14 and R15. When resistors R14 and R15 are of equal value the collector current of T5 is equal to alpha times the total collector currents of transistors T2, T3 and T4. The collector current of T5 is then a measure of temperature modified to simulate FIG. 1. The current flows into C1 in the integrator in order to integrate the function of FIG. 1 with respect to time.

Figure 3:
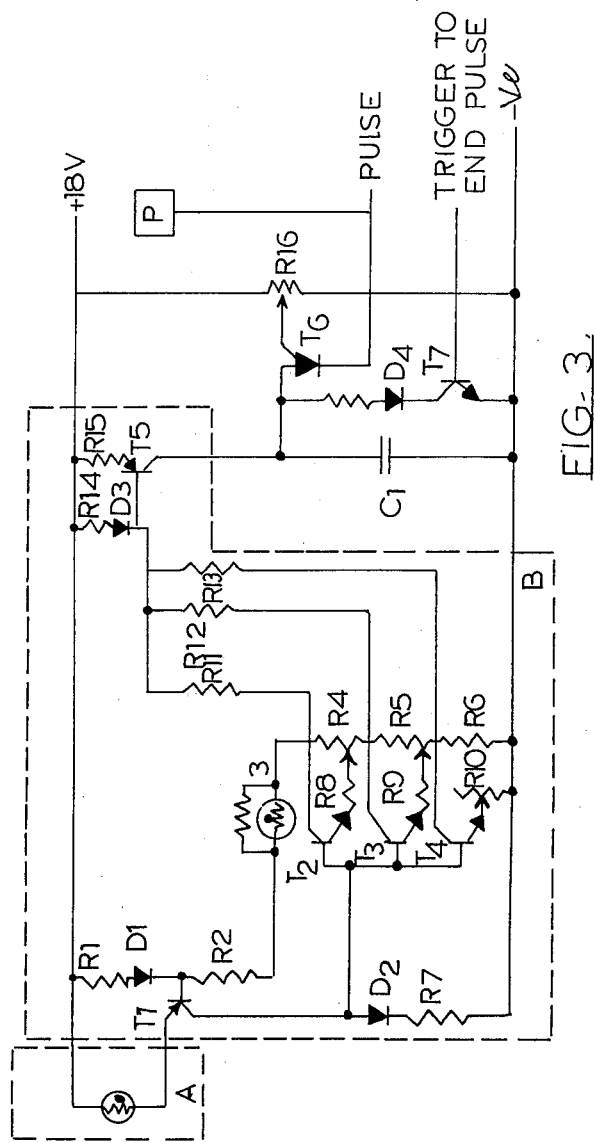
FIG. 3 is a circuit diagram of part of the temperature function integrator of FIG. 2.

BC179 transistors are used for transistors T1, T5 and diodes D1 and D3. BC109 transistors are used for transistors T2, T3 T4 and diode D2. Resistor R7 is selected to provide a suitable change in voltage with thermistor temperatures without saturating T5 or exceeding the reverse base emitter voltage ratings of T2 and T3. Resistors R4, R5, R6, R10 are the necessary combinations of fixed resistors and pre-set potentiometers to control the switching on and response of T2, T3, and T4. Resistors R14 and R15 are selected to be as large as possible in order to minimise the effects of base-emitter voltage variation in D3 and T5 without saturating T5 at any stage during the charging of C1. One megohm has been found to be a convenient value for each of these resistors. The shunted thermistor at 3 in FIG. 3 is for temperature compensation of the circuit. This is desirable because units other than the temperature sensor could be subjected to temperatures from $-20°$ C to $+20°$ C when the instrument is in use. In this range temperature drift occurs even when all transistors are diode compensated and high stability resistors are used. A properly selected thermistor and resistor at 3 in FIG. 3 provide good overall compensation. Similar compensation may be applied to other parts of the circuit; the position at 3 is most convenient. Thermal coupling of all components in unit B FIG. 3 is necessary to ensure that the temperature compensation operates satisfactorily The collector current of T5 should be as small as possible in order to minimise power consumption without falling below the minimum current required to fire silicon controlled rectifier T6. The D13 T2 programmable unijunction transistor used for T6 has minimum firing current of 0.15 microamp. A function simulating current of 0.5 microamp at 0° C is convenient to ensure that operation of the SCR does not cease at any low temperature likely to be encountered by chilled fish while the maximum current is the order of 5 microamps which is not sufficient to saturate T5 if R14 and R15 are each one megohm and the suggested voltages are used.

R16 is selected and adjusted so that the total divider resistance is of the order of one megohm and the voltage on the gate of T6 is about 10 volts. A divider resistance of one megohm is required to achieve a minimum firing current of 0.15 microamp in T6. The voltage on the gate of T6 should be low enough to ensure that T5 does not saturate. Final trimming of R16 is used to compensate for manufacturing tolerances of C1 in order to achieve a convenient rate of oscillation. T6 fires when C1 is charged to firing voltage and firing current flows through to anode-gate junction of T6. This generates one pulse of 0.1 — 0.5 second duration which is recorded on the digital pulse counter P and which may in one variation activate an audio coder and radio transmitter. At the completion of the pulse C1 is discharged through D4 and T7. Discharging C1 through T7 is desirable for control of pulse duration. D4 is to provide temperature compensation for the anode-gate voltage of T6. The use of D4 is only one way of achieving such compensation.

The time taken to charge C1 to firing voltage is inversely proportional to the charging current. C1 is selected to provide a convenient time interval between pulses and for high stability. 2 × 4.7 microforad 100 V polycarbonate capacitors have been found convenient. The pulse generation rate is inversely proportional to the time between pulses and hence directly proportional to the average current charging C1. The number of pulses registered on the counter P is then a measure of the integral of the temperature function in FIG. 1 with respect to time.

The time interval between pulses is a measure of the average modified temperature in that period and, since the period is of the order of 20–200 seconds, this interval is a useful measure of temperature for materials such as chilled fish in which temperature change is not great and is nearly constant in such a short interval. Accordingly where the instrument is used in environments when a continuous readout of temperature is useful this information can be telemetered from a number of sources by audio pulses of 0.1 - 0.5 second duration at intervals of between 20–200 seconds according to temperature. In this case the output of the circuit of FIG. 3 can go to an audio coder. This output is pulse modulation in which the time between pulses is a measure of modified temperature. Several units such as that of FIG. 2 can be used on one radio frequency and be received by one receiver. When this is the case the different units are allocated different audio frequencies so that they may be identified. The audio oscillators modulate the radio frequency transmitter E which transmits the output to a receiver F. There the audio signals can be recorded on magnetic tape and when this is played back through tuned audio channels, the separate indications of modified temperature from each of the temperature probes in use can be recorded on a strip chart recorder to give a temperature-time history. Alternatively receiver F may be associated with a temperature readout G which gives a digital or analogue indication of the pulse rate of a selected transmitter.

A series of units consisting of a multiplicity of items such as FIG. 2, all associated with one radio frequency can be installed in the fish hold or elsewhere with no connection by wire or otherwise to be brought out from the hold and to be an inconvenience to fish handlers, as well as being liable to damage.

Figure 4:
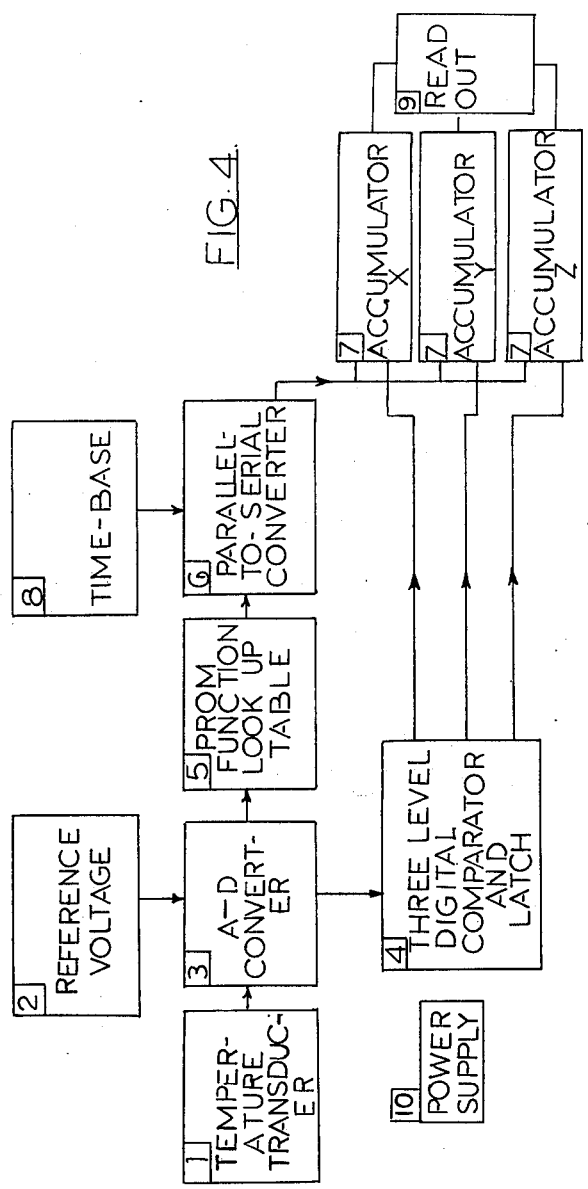
FIG. 4 is a block diagram of a second form of temperature function integrator.

The block diagram of a second and preferred form of the temperature function integrator is shown in FIG. 4. In this form of the invention the analogue output of the temperature sensor is converted to digital form and all subsequent processing is digital. The use of digital processing enables the flexibility and accuracy of the temperature function integrator to be considerably increased, since the signal modifier can take the form of a programmable read only memory (PROM) which allows the temperature-rate of deterioration relationship to be as accurate as food technology data permits. The user of a read only memory means that for every temperature value the corresponding rate of deterioration value is automatically supplied. Furthermore, since the relationship between temperature and rate of deterioration may differ between various materials, and in particular foodstuffs, the same instrument can be used for different types of food by simply plugging in a read only memory which has been programmed for that particular food.

The temperature sensor 1 used in this form of temperature function integrator is a forward biased silicon semiconductor diode. By feeding the diode with constant current the forward conduction voltage provides an electrical analogue of the temperature of the material within which the diode is implanted. As in the first form of integrator the diode is located in a suitable probe. The temperature co-efficient of this sensor is stable and very nearly linear over the temperature range of interest.

To enable an absolute measurement of temperature to be made the voltage from the diode sensor must be compared with a reference voltage. Consequently a reference voltage source 2 is provided. A precision temperature compensated zener diode (a 6.2 volt zener diode has been used in a practical realisation) is used with an active attenuator formed from an integrated circuit operational amplifier to supply a 5 volt reference signal for an analogue-to-digital (A/D) converter 3. A/D converter 3 consists of a clocked seven-bit binary counter driving an R2R resistor ladder network to generate an analogue ramp voltage. This voltage is compared with the amplified voltage from the temperature sensor diode. The output from the comparator is used to gate off the clock signal to the converter counter when the compared voltages are equal. The binary number then stored in the counter is a digital representation of the temperature of the temperature sensor. For example $-20°$ C corresponds to a binary count of 0 and $+25°$ C corresponds to a binary count of 128.

At this point in the instrument there is thus provided a binary number which corresponds to the temperature of the material within which the temperature sensor is located. According to the type of material, and in particular the type of foodstuff in question, it may be advantageous to not only obtain the integral of the modified temperature, but separate integrals for different temperature ranges. Any number of ranges may be selected, but to illustrate this concept a three-range system will be described. In order to obtain range information a three-level digital comparator and latch 4 fed by the output of the A/D converter is used. This comparator uses two diode matrix gates to determine which of the temperature ranges (in this case the regions 1, 2 or 3 of FIG. 1) the temperature indicated falls within. As the output count of the A/D converter changes these gates detect the preset binary changeover temperatures in turn. The first gate sets a first RS flip flop and the second gate sets a second RS flip flop. The states of these two flip flops are decoded to one of three bits (X, Y and Z) each of which enables a corresponding register 7. Provision is made for changing the diode gates so that the changeover temperatures may be set to any desired values.

The output of the A/D converter 3 also feeds a "function look-up table" 5 which is a programmable read only memory (PROM) which converts the binary temperature to a second binary number which corresponds to the rate of spoilage at that temperature. This number corresponds to the "modified temperature" referred to in connection with the form of the temperature function integrator already described. The PROM is programmed according to the desired temperature-rate of spoilage relation and where the temperature function integrator is to be used in conjunction with fish the PROM would be programmed according to the curve in FIG. 1. To allow the integrator to be used in conjunction with other foods or materials a number of PROMs would be provided containing the appropriate temperature-rate of deterioration data and one PROM would simply be substituted for another.

The PROM used provides 8 bits of parallel binary data and this is used to preset an 8 bit zero-stopped downcounter which forms a parallel to serial converter 6. When the PROM data is loaded into the counter an input clock pulse generator is enabled and the counter counts down until it reaches zero. This state is detected and the clock generator is stopped. The number of clock pulses required to empty the counter is proportional to the binary number provided by the PROM and thus proportional to the modified temperature. The parallel to serial converter 6 feeds (in the present example) three accumulators 7 which are binary coded decimal counters each with a capacity of 999 counts. The accumulators are each used to accumulate the temperature function data for a region of the curve in FIG. 1. The parallel-serial to converter output feeds all three counters but only one counter counts the converter output pulses since only one counter is enabled by the digital comparator 4. More than one accumulator 7 is only needed when it is required to distinguish the amount of deterioration of spoilage which has occurred in a particular temperature range. In many circumstances a single accumulator would be adequate.

Since the accumulators 7 are used to accomplish the integrating function it is necessary to provide a time base generator to activate the parallel to serial converter and thus feed pulses to the accumulators only at suitable constant time intervals i.e. the integration of the temperature function curve is made by summing the value of the curve at discrete time intervals. Bearing in mind the capacity of the counter used and the storage life of the material being assessed the time base output can be altered so that the count stored in the counter or counters provides a useful measure of deterioration of the material being assessed. In the case of fish it is useful to indicate the degree of deterioration in terms of "day equivalents at 0° C". In one preferred form of the temperature function integrator a switch enables the time base output to be altered in frequency so that the instrument has a sensitivity of either 9.99 or 99.9 day equivalents at 0° as full scale.

The number stored in the accumulator or accumulators 7 is displayed by the use of a readout 9 which would normally be a separate instrument into which a temperature function integrator would be connected following the storage or transport period and the readout would present via an LED display the accumulator count. Alternatively, in some instances it may be desirable, and possible, to check the temperature integral during the storage or transport period, in which case the readout could be made an integral part of the temperature function integrator. In the preferred form a multiplexed three digit seven segment LED display is used.

A suitable power supply 10 for this form of the invention is an eight cell nickel-cadmium battery which is regulated by a series regulator to 5 volts to operate the logic circuits. An inverter running from this regulated supply develops the voltage required by the analogue portions of the circuit and the PROM (in one working model $-12$ volts). The nickel-cadmium battery is particularly suitable because of its good low temperature performance and its ability to be recharged.

It will be appreciated that the circuits used to realize the functional blocks of FIG. 4 can take a number of forms as would be obvious to those skilled in the art.

What I claim is:

1. A temperature function integrator comprising: a transducer which senses temperature in a material being monitored and produces an electrical quantity proportional to the sensed temperature, an analogue-to-digital converter means for converting the transducer output to digital form, a digital memory loaded with temperature - rate of deterioration data which outputs in digital form the rate of deterioration corresponding to the temperature sensed at that instant, means which integrate the output from the digital memory with respect to time and which store the value of the integral upon termination of the monitoring period, and means for providing a read-out of the value of said integral as a measure of the deterioration of said material up to the time of reading.

2. A temperature function integrator according to claim 1 wherein said digital memory is a programmable read only memory.

3. A temperature function integrator according to claim 2 wherein said programmable read only memory is interchangeable to allow the temperature function integrator to be used with foods having different temperature - rate of deterioration relationship.

4. A temperature function integrator according to claim 1 wherein said integrating means comprise a parallel to serial converter, a time base which activates said converter at predetermined constant time intervals, and a digital counter which counts the output pulses from said converter.

5. A temperature function integrator according to claim 4 wherein there are a number of digital counters in parallel, and wherein there are temperature threshold detection means which enable a selected one of said counters when the temperature sensed falls within a particular predetermined temperature range.

6. A temperature function integrator according to claim 1 wherein said read-out means are located remote from the other units of the temperature function integrator and may service a plurality of such integrators.

7. A temperature function integrator according to claim 1 wherein there is provided a digital read-out for the output of said digital memory to allow continuous monitoring of rate of deterioration.

8. A temperature function integrator according to claim 7 wherein the output of said digital memory modulates a transmitter and there is provided a corresponding receiver with a digital read-out to allow continuous monitoring of rate of deterioration from one or more originating transmitters.

* * * * *